(12) United States Patent
Morishita et al.

(10) Patent No.: US 6,936,594 B1
(45) Date of Patent: Aug. 30, 2005

(54) GENE THERAPY FOR CEREBROVASCULAR DISORDERS

(75) Inventors: Ryuichi Morishita, 2-11-22-502, Miyahara, Yodogawa-ku, Osaka-shi, Osaka (JP); Toshio Ogihara, Minoo (JP)

(73) Assignees: Ryuichi Morishita, Osaka (JP); AnGes MG, Inc., Osaka (JP)

( * ) Notice: Subject to any disclaimer, the term of this patent is extended or adjusted under 35 U.S.C. 154(b) by 0 days.

(21) Appl. No.: 09/856,374
(22) PCT Filed: Sep. 18, 2000
(86) PCT No.: PCT/JP00/06347
§ 371 (c)(1),
(2), (4) Date: May 21, 2001
(87) PCT Pub. No.: WO01/21214
PCT Pub. Date: Mar. 29, 2001

(30) Foreign Application Priority Data

Sep. 21, 1999 (JP) ............................................. 11-267024
Aug. 9, 2000 (JP) ....................................... 2000-241205

(51) Int. Cl.$^7$ ......................... A61K 48/00; A61K 9/127; A01N 65/00; C12N 15/74
(52) U.S. Cl. ....................... 514/44; 424/93.1; 424/93.2; 424/93.21; 424/450; 435/320.1
(58) Field of Search .......................... 514/44; 424/93.1, 424/93.2, 93.21, 450; 435/320.1

(56) References Cited

U.S. PATENT DOCUMENTS

| 4,686,085 A | | 8/1987 | Osterholm | |
|---|---|---|---|---|
| 5,652,225 A | | 7/1997 | Isner | |
| 6,121,246 A | * | 9/2000 | Isner ............................ | 514/44 |
| 6,199,554 B1 | * | 3/2001 | Mann et al. ................. | 128/898 |
| 6,248,722 B1 | * | 6/2001 | Morishita et al. ............. | 514/44 |

FOREIGN PATENT DOCUMENTS

| EP | 0 847 757 A1 | 6/1998 | | |
|---|---|---|---|---|
| JP | 7-41429 | 2/1995 | .......... | A61K/38/22 |
| JP | 8-231416 | 9/1996 | .......... | A61K/38/22 |
| JP | 11-246434 | 9/1999 | .......... | A61K/38/22 |
| WO | 95/07709 | 3/1995 | .......... | A61K/38/18 |
| WO | WO 96/26742 A1 | 9/1996 | | |
| WO | WO 9707824 A1 * | 3/1997 | .......... | A61K/48/00 |
| WO | WO 97/14307 * | 4/1997 | | |
| WO | 97/14307 | 4/1997 | .......... | A01N/43/04 |
| WO | WO 97/30155 A1 | 8/1997 | | |
| WO | WO 99/21590 A1 | 5/1999 | | |
| WO | WO 99/36103 A1 | 7/1999 | | |

OTHER PUBLICATIONS

Yonemitsu et al, Gene Ther 1997;4:631–8.*
Wang et al, Biochem Biophy Comm 1998;244:449–54.*
Rosengart et al, Circulation 1999;100:468–74.*
Furlan et al, Hum Gene Ther 1998;9:2605–17.*
Ghodsi et al, Hum Gene Ther 1998;9:2331–40.*
de Lecinana et.al.; Cerebral ischemia: from animal studies to clinical practice. Should the methods be reviewed?, 2001, Cerebrovasc Dis 11: 20–30.*
Orkin et.al.; Report and Recommendations of the Panel to Assess the NIH Investment in Research on Gene Therapy, 1995: 1–37.*
Verma et.al.; gene therapy– promises, problems and prospects, 1997, Nature, vol. 389: 239–242.*
Rozenberg et.al.; Alternative gene delivery, 2001,S.T.P. Pharma Sciences 11: 21–30.*
Nishikawa et.al.; Nonviral Vectors in the New Millennium: Delivery Barriers in Gene Transfer, 2001, Human Gene Therapy 12: 861–870.*
Balicki et.al.; Reviews in Molecular Medicine, 2002, Medicine 81: 69–86.*
Castro et.al.; Gene therapy for Parkinson's disease: recent achievements and remaining challenges, 2001, History and Histopathology 16: 1225–1238.*
Chinese Office Action for Chinese Patent Application No. 00802004.3 dated Feb. 4, 2004.
John Laterra, et al., "Scatter Factor/Hepatocyte Growth factor Gene Transfer Enhances Glioma Growth and Angiogenesis In Vivo", Laboratory Investigation, vol. 76, No. 4, pp. 565–577, 1997 and PubMed Abstract.
International Search Report.
Adventure in Gene Theray: "MEDGENE" as the First Academic Genetic Bioventure, BIOJAPAN 2000 Symposium Proceedings, pp. 183–193 (Presented on Sep. 27, 2000).
International Search Report Dec. 2000.
Adventure in Gene Theray: "MEDGENE" as the First Academic Genetic Bioventure, BIOJAPAN 2000 Symposium Proceedings, pp. 183–193 (Presented on Sep. 27, 2000).
Taiwanese Office Action, Feb. 3, 2005.
Papavassiliou E., et al., "Vascular endothelial growth factor (vascular permeability factor) expression in injured rat brain." J Neurosci Res., Aug. 15, 1997, vol. 49(4) pp. 451–460.
Issa R., et al., "Vascular endothelial growth factor and its receptor, KDR, in human brain tissue after ischemic stroke." Lab Invest. Apr., 1999, vol. 79(4), pp. 417–425.

\* cited by examiner

Primary Examiner—Q. Janice Li
(74) Attorney, Agent, or Firm—Sughrue Mion, PLLC

(57) ABSTRACT

By introducing hepatocyte growth factor (HGF) gene and/or vascular endothelial growth factor (VEGF) gene into the subarachnoid space in humans, cerebrovascular disorders such as cerebrovascular obstruction, cerebral infarction, cerebral thrombosis, cerebral embolism, stroke, cerebral bleeding, moyamoya disease, cerebrovascular dementia, and Alzheimer's dementia can be effectively treated or prevented.

5 Claims, 16 Drawing Sheets

*β-Gal stain*

*Delayed neuronal death*

Sham ope. 7days

Vehicle 4days

Vehicle 7days

*HE stain*

*HGF injection*

Post HGF gene 4days        Post HGF gene 7days

Pre HGF gene 7days         r-HGF 30 μg 7days

*C-Met*

*TUNEL*

*DND 7days*

*Post HGF gene 7days*

*Pre HGF gene 7days*

*bcl-xL* sham.

post HGF 4days post HGF 7days

HSP 70

*post HGF 7days*

*HSP70*

Sham.

Post HGF 7D

GENE THERAPY FOR CEREBROVASCULAR DISORDERS

TECHNICAL FIELD

The present invention relates to novel gene therapy agents for treating or preventing cerebrovascular disorders, and novel methods for administration of said gene therapy agents. More preferably, the present invention relates to therapeutic or preventive agents for cerebrovascular disorders comprising hepatocyte growth factor (HGF) gene and/or vascular endothelial growth factor (VEGF) gene as an active ingredient, or novel administration methods comprising administering said therapeutic or preventive agents to the subarachnoid space.

BACKGROUND ART

Cerebral obstructive diseases, moyamoya disease and the like caused by atherosclerosis in the cerebral artery often result in chronic reduction in cerebral blood flow. This state may lead not only to the subsequent cerebral ischemic events but also to neuropathological changes including dementia (Stroke 25:1022–1027, Stroke 29:1058–1062 (1998)); Stroke 24:259–264 (1993); Ann. N. Y. Acad. Sci. 695:190–193 (1993)). However, no effective methods for improving the reduced blood flow in these cerebrovascular disorders have been established yet. It is known that in ischemic attacks, active angiogenesis takes place specifically at the peripheral regions of the ischemia, and this is involved in prolonged survival in humans (Stroke 25:1794–1798 (1994)). Thus, angiogenesis has been considered to play an important role in recovery from cerebral ischemia and prevention of future attacks.

The development of new blood vessels and angiogenesis are triggered concurrently with the activation of the endothelial cell. A growth factor that has been shown not only to stimulate angiogenesis in vivo, but also to be mitogenic in vitro to the endothelial cell is called "angiogenic growth factor."

The therapeutic involvement of angiogenic growth factor was first described in literature by Folkman et al. (N. Eng. J. Med. 285:1182–1186 (1971)). Subsequent research confirmed that recombinant angiogenic factor such as fibroblast growth factor (FGF) family (Science 257:1401–1403 (1992); Nature 362:844–846 (1993)), endothelial growth factor (J. Surg. Res. 54:575–583 (1993)), and vascular endothelial growth factor (VEGF) may be used to promote and/or enhance the development of collateral circulation shunt in animal models of myocardial and hindlimb ischemia (Circulation 90:II-228–II-234 (1994)). Furthermore, the present inventors have found that HGF acts as a endothelium-specific growth factor as does VEGF (J. Hypertens. 14:1067–1072 (1996)).

A strategy as described above that employs angiogenic growth factor to treat vascular disorders is called "therapeutic angiogenesis." More recently, the strategy has been applied to ischemic diseases in humans. However, the effectiveness of the strategy in cerebral ischemia has not been known so far.

Hepatocyte growth factor (HGF) is a pleiotropic cytokine that exhibits mitogenic, motility promoting, and morphogenic activity on a variety of cells (Nature 342:440–443 (1989)).

Effects of HGF on the brain has been reported as follows. Thus, it is known that HGF in combination with c-Met/HGF receptor of a transmembrane tyrosine kinase is expressed at various regions in the brain, and the operative linkage of HGF and c-Met enhances the survival of neurons in the primary culture of hippocampus, and induces neutrite elongation in the development in vitro of neurons (J. Cell. Biol. 126:485–494 (1994); Japanese Unexamined Patent Publication (Kokai) No. 7-89869). Recently, it has been reported that HGF is induced in neurons in ischemia (Brain Res. 799:311–316 (1998)), that recombinant HGF has a neuroprotective effect on delayed neuronal death after ischemia in the hippocampus, and that the continuous injection of recombinant HGF into the brain was effective in reducing the size of infarction (J. Cereb. Blood Flow Metab. 18:345–348 (1998)). These findings suggest that HGF acts as an important neurotrophic factor in cerebral ischemia.

On the other hand, vascular endothelial growth factor (VEGF) is a dimeric glycoprotein mitogenic to the endothelial cell and has an ability of enhancing vascular permeability. VEGF has a direct and specific mitogenic effect on the endothelial cell (Biochem. Biophys. Res. Commun. 161:851–858 (1989)). The binding sites of VEGF including tyrosine kinase receptor Flt, Flk-1, and KDR occur on the endothelial cell but not on other cell types, thereby limiting the effect of VEGF to the endothelial cell.

With respect to the effect of VEGF on the brain, it has been reported that VEGF in the central nervous system is rapidly induced by ischemic disorders in the brain (Mol. Cell. Biol., 16:4604–4613 (1996)), and that the administration of recombinant VEGF to the brain surface effectively reduced the amount of infarction (J. Cereb. Blood Flow Metab. 18:887–895 (1998)). Details thereof has not been known, however.

In another aspect, in addition to the above-mentioned actions of HGF and VEGF, these factors are potent angiogenic growth factors as mentioned above (J. Cell. Biol. 119:629–641 (1992)); Biochem. Biophys. Res. Commun. 161:851–858 (1989)). Ischemic attacks are known to give rise to active angiogenesis in the periphery of ischemia, which is related to prolonged survival of humans (Stroke 25:1794–1798 (1994)). Thus, angiogenesis is thought to play an important role in recovery from cerebral ischemia and in prevention of future attacks. However, it is not known whether therapeutic angiogenesis using recombinant HGF or VEGF is actually feasible for cerebral ischemia etc. Furthermore, recombinant angiogenic growth factors rapidly disappear from the brain and thus require continuous injection into the brain, which procedure is rather dangerous and impractical in the clinical settings. Thus, it would be reasonable if the technique of gene introduction is used to express and secrete angiogenic growth factors in ischemic brain and its periphery on a continual basis. There are no examples so far in which HGF gene or VEGF gene has been applied (gene therapy) to ischemic disorders in the brain, and possibly because of its unique feature of the brain tissue, there are no suggestions made on the applicability thereof.

DISCLOSURE OF THE INVENTION

The present invention relates to novel gene therapy agents for treating or preventing cerebrovascular disorders, and novel methods for administration of said gene therapy agents. More preferably, the present invention relates to novel agents for treating and preventing cerebrovascular disorders comprising hepatocyte growth factor (HGF) gene and/or vascular endothelial growth factor (VEGF) gene as an active ingredient, or novel administration methods comprising administering said therapeutic or preventive agents to the subarachnoid space.

The present inventors investigated in vivo whether the introduction of HGF gene and VEGF gene can induce angiogenesis on the surface of an ischemic brain. As a result, we have revealed that: (a) after the transfection of HGF gene or VEGF gene, these proteins are detected in the brain over a prolonged period of time, (b) therapy with HGF gene or VEGF gene transfection can induce angiogenesis on the surface of an ischemic brain, (c) the transfection of HGF gene or VEGF gene is effective In treating reduced blood flow in the brain caused by vascular obstruction, and (d) the therapy is also useful when performed before obstruction. Furthermore, we have also demonstrated that the introduction of these genes can be more effectively attained by a novel method of administration i.e., introduction into subarachnoid space.

In addition, the present inventors have found that delayed neuronal death due to ischemia in the hippocampus CA-1 region can be suppressed by the introduction of HGF gene.

Based on the foregoing findings, the present invention was completed.

Thus, the present invention provides the inventions described in the following (1) to (23).

(1) A therapeutic and preventive agent for cerebrovascular disorders comprising HGF gene and/or VEGF gene as an active ingredient;

(2) The therapeutic or preventive agent in the above (1) wherein cerebrovascular disorders are cerebrovascular obstruction, cerebral infarction, cerebral thrombosis, cerebral embolism, stroke, cerebral bleeding, moyamoya disease, cerebrovascular dementia, Alzheimer's dementia, and sequelae of cerebral bleeding or cerebral infarction;

(3) A therapeutic or preventive agent for reduced blood flow in the brain comprising HGF gene and/or VEGF gene as an active ingredient;

(4) A promoting agent for angiogenesis in the brain comprising HGF gene and/or VEGF gene as an active ingredient;

(5) A suppressing agent for neuronal death in the brain comprising HGF gene as an active ingredient;

(6) The suppressing agent of the above (5) wherein neuronal death in the brain is delayed neuronal death caused by cerebral ischemia;

(7) A suppressing agent for apoptosis of nerve cells in the brain comprising HGF gene as an active ingredient;

(8) The agent in any of the above (1)–(7) which comprises HGF gene and/or VEGF gene as an active ingredient and which is to be used in combination with HGF protein and/or VEGF protein;

(9) The agent of the above (8) which comprises HGF gene as an active ingredient and which is to be used in combination with HGF protein;

(10) The agent in any of the above (1)–(9) wherein HGF gene and/or VEGF gene are in the form of HVJ-liposome;

(11) The agent in any of the above (1)–(10) to be administered into the subarachnoid space;

(12) A method of producing the agent in any of the above (1)–(11) comprising blending HGF gene and/or VEGF gene with a pharmaceutically acceptable solvent;

(13) A therapeutic or preventive method for cerebrovascular disorders comprising introducing HGF gene and/or VEGF gene into humans;

(14) A therapeutic or preventive method for reduced blood flow comprising introducing HGF gene and/or VEGF gene into humans;

(15) A method of promoting cerebral angiogenesis comprising introducing HGF gene and/or VEGF gene into humans;

(16) A method of suppressing neuronal death in the brain comprising introducing HGF gene into humans;

(17) A method of suppressing apoptosis of nerve cells in the brain comprising introducing HGF gene into humans;

(18) The method in any of the above (13)–(17) comprising administering HGF gene and/or VEGF gene into the subarachnoid space in humans;

(19) The method in any of the above (13)–(18) comprising administering HGF protein and/or VEGF protein together with the introduction of HGF gene and/or VEGF gene;

(20) The method in the above (19) comprising administering HGF protein together with the introduction of HGF gene;

(21) Use of HGF gene and/or VEGF gene in the manufacture of a therapeutic or preventive agent for cerebrovascular disorders;

(22) Use of HGF gene and/or VEGF gene in the manufacture of a therapeutic or preventive agent for reduced blood flow in the brain;

(23) Use of HGF gene and/or VEGF gene in the manufacture of a promoting agent for angiogenesis in the brain;

(24) Use of HGF gene in the manufacture of a suppressing agent for neuronal death in the brain; and

(25) Use of HGF gene in the manufacture of a suppressing agent for apoptosis of nerve cells in the brain.

BEST MODE FOR CARRYING OUT THE INVENTION

Figure 1:
FIG. 1 is a photograph of morphology of an organism exhibiting the expression of β-gal (β-galactosidase) on the brain surface. Bottom, the injection of HVJ-liposome (1 ml) into the internal carotid artery; middle, the injection of HVJ-liposome (100 μl) Into the cisterna (subarachnoid space); upper, the injection of HVJ-liposome (20 μl) into the lateral ventricle. n=4 for each group.

As used herein "HGF gene" means a gene that can express HGF (HGF protein). Specifically, there can be mentioned one in which cDNA of HGF as described in Nature 342:440 (1989); Patent Publication No., 2777678; Biochem. Biophys. Res. Commun. 163:967 (1989); and Biochem. Biophys. Res. Commun. 172:321 (1990) was integrated into a suitable expression vector (nonviral vector, viral vector) as described below. The base sequence of cDNA encoding HGF has been described in the above literature and also been registered at databases such as Genbank. Thus, based on such sequence information, a suitable DNA portion is used as a PCR primer; for example, by performing a RT-PCR reaction on mRNA derived from the liver or leukocytes, cDNA of HGF can be cloned. Such cloning can easily be performed by a person skilled in the art according to a basic textbook such as Molecular Cloning 2nd Ed., Cold Spring Harbor Laboratory Press (1989).

Furthermore, the HGF gene of the present invention is not limited to those described above, but any gene may be used as the HGF gene of the present invention as long as the protein expressed by said gene can act in virtually the same manner as HGF. Thus, from among 1) DNA that hybridizes to said cDNA under a stringent condition and 2) DNA encoding a protein comprising an amino acid sequence in which one or a plurality of (preferably several) amino acids have been substituted in, deleted from, and/or added to the amino acid sequence of the protein encoded by said cDNA and the like, those that encode a protein having an action as HGF are encompassed in the category of HGF gene of the present invention. DNA in the above 1) and 2) may be easily obtained by site-directed mutagenesis, a PCR method, or a standard hybridization method and the like, and specifically they may be performed with reference to a basic textbook such as the above Molecular Cloning etc.

As used herein "VEGF gene" means a gene that can express VEGF (VEGF protein). Thus, there can be illustrated one integrated into a suitable expression vector (nonviral vector, viral vector) as described below. By selective splicing of VEGF gene at transcription in humans, the presence of 4 subtypes (VEGF121, VEGF165, VEGF189, VEGF206) have been reported (Science 219:983 (1983); J. Clin. Invest. 84:1470 (1989); Biochem. Biophys. Res. Commun. 161:851 (1989)). According to the present invention, any of these VEGF genes can be used, but from the viewpoint of being biologically most potent, VEGF165 gene is most preferred. Furthermore, as in the case of the above HGF, modified versions of these VEGF genes are encompassed in the category of the VEGF gene of the present invention as long as they encode a protein having an activity as VEGF.

Said VEGF gene, as in the case of HGF gene, may be easily cloned by a person skilled in the art based on sequences as previously described (for example, Science 246:1306 (1989)) and sequence information registered in databases, and their modification can also be easily performed.

According to the present invention, it was demonstrated for the first time that cerebrovascular disorders can be treated or prevented with HGF gene or VEGF gene. Thus, the present invention revealed, for the first time, that (a) after the transfection of HGF gene or VEGF gene, these proteins are detected in the brain over a prolonged period of time, (b) by treatment using HGF gene or VEGF gene transfection, angiogenesis can be induced on the surface of an ischemic brain, (c) the transfection of HGF gene or VEGF gene is effective in treating reduced blood flow in the brain caused by obstruction in the blood vessels, and (d) this treatment method is also effective when performed before obstruction. Thus, HGF gene and VEGF gene may be effectively used as a therapeutic or preventive agent for various cerebrovascular disorders such as disorders resulting from cerebral ischemia, disorders associated with reduced blood flow in the brain, disorders for which improvement is expected by promoting angiogenesis in the brain, and the like.

Specifically they are effectively used as therapeutic or preventive agents (hereinafter, the therapeutic or preventive agents of the present invention are simply designated as gene therapy agents) for cerebrovascular obstruction, cerebral infarction, cerebral thrombosis, cerebral embolism, stroke (including subarachnoid bleeding, transient cerebral ischemia, cerebral atheroscrelosis), cerebral bleeding, moyamoya disease, cerebrovascular dementia, Alzheimer's dementia, sequelae of cerebral bleeding or cerebral infarction, and the like.

Furthermore, the present inventors have found that delayed neuronal death due to ischemia in the hippocampus CA-1 region is suppressed by the introduction of HGF gene, that is. HGF gene has an effect of suppressing neuronal death in the brain. We have also demonstrated that this effect is based on the c-Met-mediated apoptosis-suppressing effect of nerve cells.

The hippocampus CA-1 region as used herein is a region that is densely populated with nerves and a region that is susceptible to neuronal death by cerebral ischemia. Such HGF gene has been found to be able to treat and prevent cerebrovascular disorders based on the both of the angiogenic effect (suppression of reduced blood flow) and the nerve cell protective effect.

Since HGF gene has c-Met-mediated nerve cell protecting effect as described above, it can be effectively used as a therapeutic or preventive agent for neurodegenerative diseases such as Alzheimer's disease, Alzheimer's senile dementia, amyotrophic lateral sclerosis, or Parkinson's disease.

In accordance with the present invention, HGF gene and VEGF gene may be used alone or in combination with each other. They can also be used in combination with the gene of other vascular endothelial growth factors. Furthermore, HGF gene and/or VEGF gene may be used in combination with HGF protein and/or VEGF protein. Preferred are a combination of HGF gene and HGF protein or of VEGF gene and VEGF protein, more preferably of HGF gene and HGF protein. See Example 4 below for details.

HGF protein as used herein may be obtained by any method as long as it has been purified to the extent it may be usable as a pharmaceutical drug. Commercially available products (for example Toyoboseki k. k., Code No. HGF-101, etc.) may also be used. cDNA of HGF obtained by cloning mentioned above is inserted into any suitable expression vector, which is introduced into a host cell to obtain a transformant, from the culture supernatant of which transformant may be obtained recombinant HGF protein of interest (see, for example, Nature 342:440 (1989): Patent Publication No. 2777678). VEGF protein can also be obtained in a similar manner.

Then, a method of gene introduction, form of introduction, amount to be introduced and the like for use in gene therapy of the present invention are explained.

When a gene therapy agent comprising the above gene as an active ingredient is to be administered to patients, the dosage regimens are roughly divided into two: a case in which a nonviral vector is used, and a case in which a viral vector is used. The methods of preparation and administration thereof are explained in detail in experimental manuals (Separate volume of Experimental Medicine, Basic Technology in gene therapy, Yodosha (1996); Separate volume of Experimental Medicine, Experimental Methods in Gene Introduction and Expression Analysis, Yodosha (1997); Handbook for Development and Research of Gene Therapy, edited by Japan Society of Gene Therapy, NTS (1999)). This will be explained in specific terms below.

A. When a Nonviral Vector is Used

Using a recombinant expression vector in which a gene of interest has been integrated into a commonly used gene expression vector may be used to introduce the gene of interest into cells or tissue by the following method etc.

As a method of gene introduction into cells, there can be mentioned the lipofection method, the calcium phosphate co-precipitation method, the DEAE-dextran method, direct DNA introduction methods using micro glass tubes, and the like.

As a method of gene introduction into the tissue, a recombinant expression vector may be incorporated into the cell by subjecting any of a method of gene introduction with internal type liposome, a method of gene introduction with electrostatic type liposome, the HVJ-liposome method, the improved HVJ-liposome method (HVJ-AVE liposome method), the receptor-mediated gene introduction method, a method of introducing DNA molecules together with carriers (metal particles) by a particle gun, a method of directly introducing naked-DNA, a method of introduction with positively-charged polymers and the like.

Among them, HVJ-liposome is a fusion product prepared by enclosing DNA into liposome made of lipid bilayer, which was fused to inactivated Sendai virus (Hemagglutinating virus of Japan: HVJ). The HVJ-liposome method is characterized by a very high fusing activity with the cell membrane compared to the conventional liposome method, and is a preferred mode of introduction. For the method of preparing HVJ-liposome, see, for details, the literature (Separate volume of Experimental Medicine, Basic Technology in gene therapy, Yodosha (1996); Experimental Methods in Gene Introduction and Expression Analysis, Yodosha (1997); J. Clin. Invest. 93:1458–1464 (1994); Am. J. Physiol. 271:R1212–1220 (1996)) and the like, and experimental examples described below for details. As HVJ, the Z strain (available from ATCC) is preferred, but other HVJ strains (for example, ATCC VR-907 and ATCC VR-105) may also be used.

Furthermore, the method of directly introducing naked-DNA is the most simple method among the methods described above, and in this regard a preferred method of introduction.

Expression vectors as used herein may be any expression vectors as long as they permit the expression in vivo of the gene of interest, and include, for example, expression vectors such as pCAGGS (Gene 108:193–200 (1991)), pBK-CMV, pcDNA3.1, pZeoSV (Invitrogen, Stratagene) and the like.

B. When a Viral Vector is Used

Representative methods use, as viral vectors such as recombinant adenovirus, retrovirus and the like. More specifically, the gene of interest can be introduced into DNA virus or RNA virus such as detoxified retrovirus, adenovirus. adeno-associated virus, herpesvirus, vaccinia virus, poxvirus, poliovirus, Sindbis virus, Sendai virus, SV40, human immunodeficiency virus (HIV) and the like, which is then infected to the cell to introduce the gene into the cell.

Among the above viral vectors, the efficiency of infection is known to be the highest with adenovirus than with other viral vectors. In this regard, it is preferred to use an adenovirus vector system.

As methods of introducing a gene therapy agent into a patient, there are an in vivo method that permits direct introduction of the gene therapy agent into the body, and an ex vivo method in which certain cells are removed from a human and a gene therapy agent is introduced into said cells, which are then returned into the body (Nikkei Science, April 1994 issue pp. 20–24; Monthly Yakuji, 36(1):23–48 (1994); Supplement to Experimental Medicine 12(15) (1994); Handbook for Development and Research of Gene Therapy, edited by Japan Society of Gene Therapy, NTS (1999)). According to the present invention, the in vivo method is preferred.

Sites for administration to patients are selected depending on the disease, disease state and the like to be treated. For example, in addition to making a hole directly into the cranium and introducing the gene therethrough, there is administration to the lateral ventricle or administration to the subarachnoid space. Among them, administration to the subarachnoid space is a novel and efficient method of administration that was disclosed in the present invention. The administration to the subarachnoid space is desired when it is intended to treat the disease based on the original purpose. i.e. when reduced blood flow in the brain is treated by angiogenesis and/or by suppressing neuronal death in the brain.

Dosage forms may take various forms according to various administration regimens described above (for example, liquids). When, for example, an injection containing the gene as an active ingredient is to be used, said injection may be prepared according to a standard method. For example, after dissolving in a suitable solvent (a buffer such as PBS, physiological saline, sterile water, etc.), it is filter-sterilized with filter as needed, and then filled into sterilized containers. Commonly used carriers etc. may be added to the injection. In liposomes such as HVJ-liposome, they may take the form of suspensions, frozen formulations, centrifugation-concentrated frozen formulations and the like.

In order to facilitate delivery of the gene into the periphery of a lesion site, a sustained release preparation (minipellet formulation, etc.) may be prepared and implanted near the affected region, or it can be administered to the affected area continuously and gradually using an osmotic pump etc.

The content of DNA in the formulation may be controlled as appropriate depending on the disease to be treated, age and weight of the patient, etc., and usually it is in the range of 0.0001–100 mg, preferably 0.001–10 mg, as the DNA of the present invention, which is preferably given every few days to every few months.

The present invention will now be specifically explained with reference to the following examples. It should be noted, however, that the present invention is not limited by these examples in any way.

Experiment I.

A Study on Angiogenesis and Effect of Improving Blood Flow in the Brain with HGF Gene and VEGF Gene Materials and Experimental Methods 1) Ligation of the Bilateral Carotid Arteries Male Sprague Dawley rats (350–400 g; Charles River Japan, Atsugi city, Japan) were anesthetized with pentobarbital sodium (50 mg/kg, intraperitoneal), and were allowed to breathe spontaneously during surgery. By midline neck incision, the bilateral carotid arteries were exposed, and were tightly ligated by 2-0 silk.

2) Preparation of HVJ-liposome Complex

The method used to prepare HVJ-liposome is as previously described (J. Clin. Invest. 93:1458–1464 (1994); Am. J. Physiol. 271:R1212–1220 (1996)). Briefly, phosphatidyl serine, phosphatidyl choline, and cholesterol were mixed at a weight ratio of 1:4.8:2. Tetrahydrofuran was removed by rotary evaporator to allow the lipid mixture (10 mg) to deposit on the side wall of the flask. The dried lipid was hydrated in 200 μl of a balanced salt solution (BSS: 137 μM NaCl, 5.4 μM KCl, 10 μM Tris-HCl, pH 7.6) having an expression vector in which the gene of interest had been inserted. Liposomes in the control group contain an expression vector having no gene of interest (BSS 200 μl). Liposomes were prepared by shaking and ultrasonication.

Purified HVJ (Z strain) was inactivated by UV irradiation (110 erg/mm$^2$ per second) for 3 minutes immediately prior to use. A liposome mixture (0.5 ml containing 10 mg of lipid) was mixed with HVJ (10,000 hemagglutination units in a total volume of 4 ml). The mixture was incubated at 4° C. for 5 minutes, and then at 37° C. for 30 minutes while shaking gently. Free HVJ was removed from the HVJ-liposome by sucrose density gradient centrifugation. The uppermost layer of the sucrose gradient was collected and used. The final concentration of plasmid DNA was equal to 20 μg/ml when calculated as previously reported (J. Clin. Invest. 93:1458–1464 (1994); Am. J. Physiol. 271:R1212–1220 (1996)). The method of preparation has been optimized so as to attain the maximum transfection efficiency.

3) In vivo Gene Introduction

In order to establish an efficient method of in vivo gene introduction, we have tested three different methods to deliver plasmid that formed a complex with the HVJ-liposome: 1) direct introduction into the internal carotid artery, 2) injection into the lateral ventricle, and 3) injection into the cisterna (subarachnoid space).

For the introduction into the internal carotid artery, male Sprague Dawley rats (350–400 g) were anesthetized with pentobarbital sodium (50 mg/kg, intraperitoneal), and incision was made to the left common carotid artery, into which a polyethylene catheter (PE-50, Clay Adams, Parsippany, N.J.) was introduced (Rakugi et al.). The distal region of the external carotid artery was isolated for a short time by closing with ligature temporarily. The HVJ-liposome complex (1 ml) was injected into the external carotid artery region. After injection, the injection canula was removed and the ligature was loosened to recover blood flow into the common carotid artery.

For injection into the lateral ventricle, the anesthetized rats were placed in a stereotaxic apparatus (Narishige Scientific Instrument Laboratory, Tokyo, Japan) to expose the cranium. A stainless steel canula (30 gauge; Becton Dickinson, Franklin Lakes, N.J.) with a specifically designed Teflon connector (FEP tube, Bioanalytical Systems, West Lafayette, Ind.) was introduced into the left lateral ventricle ad previously described (Am. J. Physiol. 271:R1212–1220 (1996)). The stereotaxic coordinate was as follows: behind the bregma, 1.3 mm; side of the midline, 2.1 mm; and under the cranial surface, 3.6 mm. The HVJ-liposome complex was injected to the lateral ventricle (20 μl). After the injection of the HVJ-liposome complex, the injection canula was removed. No behavioral changes such as spasm in the extremities and abnormal movement were observed in any animal that received injection.

For injection into the subarachnoid space, the head of each animal was fixed at a horizontal position, and the atlantoccipital membrane was exposed by the midline incision of the occipital bone. A stainless steel canula (27 gauge; Becton Dickinson, Franklin Lakes, N.J.) was introduced into the subarachnoid space. The position of the canula was confirmed, and in order to avoid increases in intracranial pressure, 100 μl of cerebrospinal fluid was removed. Then the HVJ-liposome solution (100 μl: 100 μg/ml) was carefully injected into the cisterna (subarachnoid space) over more than one minute. Then the animal was placed with the head down for 30 minutes. A preventive dosage of antibiotics (30,000 U penicillin) was administered to complete the sterile procedure.

4) Laser Doppler Imaging

Using a laser Doppler imager (LDI), continuous blood flow was recorded for two weeks after the surgery. The LDI system (Moore Instruments Ltd., Devon, UK) has a 2 W built-in helium-neon laser in order to generate a beam that continuously scans to a depth of 600 μm of the tissue surface of 12×12 cm. During scanning, blood cells moving in the blood system change the frequency of the incident light according to the Doppler principle. A photodiode collects the scattered light in the opposite direction, and thereby variation in the original light strength are converted into voltage variation in the range of 0–10 V. A perfusion output value at 0 V was graduated at 0% perfusion, and 10 V was graduated at 100% perfusion. After scanning is complete and the scattered light in the opposite direction is collected from all measurement sites, color-coded images showing blood flow are displayed on a television monitor. Perfusion signals are divided into six different sections, each being displayed as a distinct color. The reduced blood flow or no perfusion is indicated by dark blue, while the maximum perfusion is displayed as red.

Using the LDI, perfusion at the brain surface was recorded before, immediately after, 7 and 14 days after obstruction. Along the midline incision on the scalp, a bone window of 12×12 cm was made using an electric drill. On this bone window, continuous measurement values were obtained. Color-coded images were recorded, and analysis was performed by calculating mean perfusion values for each rat. In order to consider variables containing ambient light and temperature, calculated values of perfusion were expressed as ratios of the brain after (ischemia) to before (nontreatment).

5) Histopathological Examination

After fixing in a 3% paraformaldehyde/20% sucrose solution for one day, 25 μm frozen sections of coronal plane were made for every 100 μm for use in X-gal staining. The sections were stained with X-gal to identify stained neurons that are expressing β-galactosidase. 25 μm frozen sections of coronal plane were made for every 100 μm for use in alkaline phosphatase (ALP) staining. These sections were incubated together with PBS containing 0.3% hydrogen peroxide to decrease endogenous peroxidase activity, and then were incubated with primary antibody diluted in PBS containing 10% equine serum or a lectin at room temperature for 60 minutes. After washing three times in a Tris buffered saline containing 2% equine serum, the biotin-tagged secondary antibody compatible with the species and then avidin-biotin peroxidase complex (Vectastain ABC kit, PK6100, Vector laboratories, Burlingame, Calif.) were incubated. Antibody binding was visualized using diaminobenzidine. Primary antibody was omitted and stained with unrelated immunoglobulin compatible with the type and class in order to use as a negative control for each antibody.

6) ELISA Method on HGF and VEGF in the Cerebrospinal Fluid (CSF)

CSF (100 μl) obtained from rats before, 7 and 14 days after the obstruction of the bilateral carotid arteries was used in the experiments. Rat and human HGFs were determined by an ELISA kit (Institute of Immunology, Tokyo), and human VEGF was also determined by an ELISA kit (R&D systems, Minneapolis, Minn.).

7) Experimental Materials cDNA of human HGF (U.S. Pat. No. 2777678) was cloned by a standard method, which was inserted into an expression vector pcDNA (manufactured by Invitrogen) and used as human HGF gene.

cDNA of human VEGF165 (Science 246:1306 (1989)) was cloned by a standard method, which was inserted into an expression vector pUC-CAGGS and used as human VEGF gene.

Using a recombinant expression vector in which cDNA of human HGF (U.S. Pat. No. 2,777,678) was inserted into an expression vector pcDNA (manufactured by Invitrogen), Chinese hamster ovary cells (ATCC) or C-127 cells (ATCC) were transfected, and from the culture medium thereof human recombinant HGF was purified by a standard method and used.

Based on the above materials and experimental method, the following Examples 1–4 were performed.

EXAMPLE 1
Effect of the HVJ-liposome Delivery System on In vivo Transfection of β-galactosidase Gene As a gene to be introduced, β-galactosidase gene (manufactured by Invitrogen, concentration in HVJ-liposome: 20 µg/ml) was used to prepare HVJ-liposome as described in the above materials and experimental method.

Figure 2:
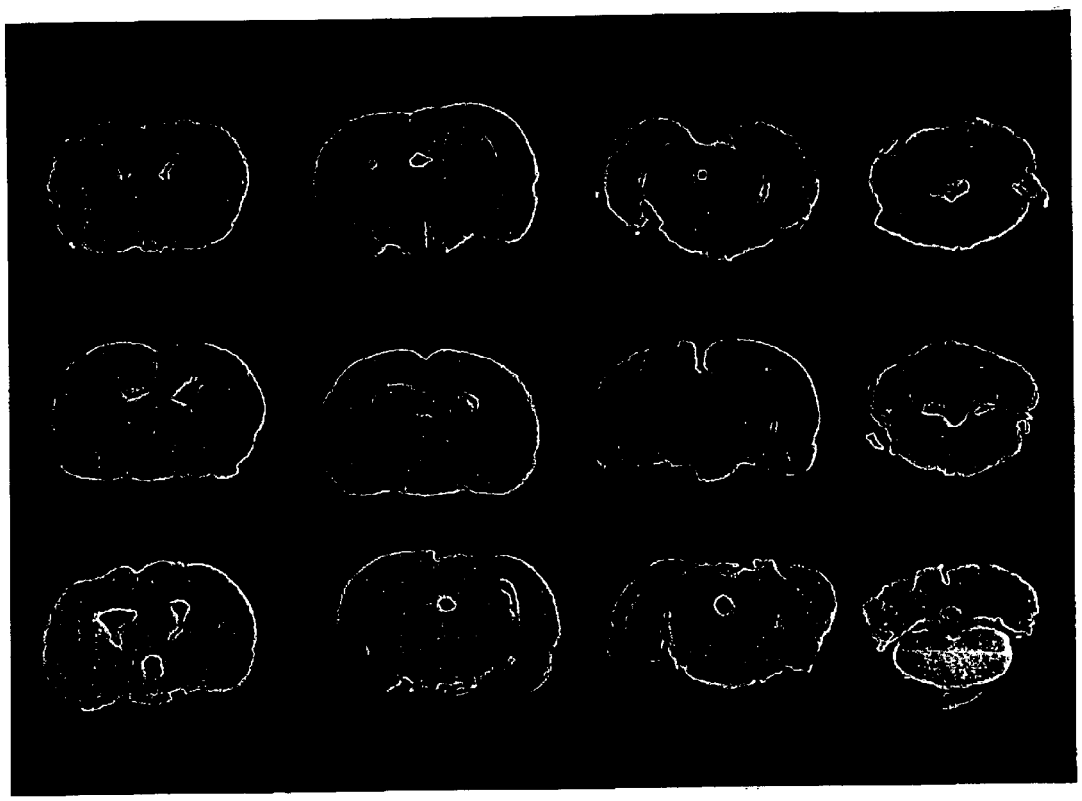
FIG. 2 is a photograph of morphology of an organism exhibiting the expression of β-gal (β-galactosidase) in the brain. Left, the injection into the internal carotid artery; middle, the injection into the lateral ventricle; right, injection into the cisterna (subarachnoid space).

First, the HVJ-liposome complex was injected directly into the internal carotid artery and was allowed to reach the brain. However, in the intraarterial injection in the above carotid artery, little expression in the brain or microvascular endothelial cells was generated on day 3 and 7 after the injection (data not shown). Therefore, HVJ-liposome was injected into the lateral ventricle and the subarachnoid space. The injection of β-galactosidase gene by the HVJ-liposome method gave rise to marked expression of β-gal on day 3 and 7 after the injection (FIG. 1 and FIG. 2). When injected into the lateral brain, β-gal expression was mainly observed in the lateral ventricle and the perichoroidal plexus. In contrast, when injected into the subarachnoid space, β-gal expression was observed on the brain surface. The foregoing result revealed that injection into the subarachnoid space is better when the reduced blood flow in the brain is to be treated by angiogenesis.

EXAMPLE 2
In vivo Transfection of HGF Gene and VEGF Gene

Figure 3:
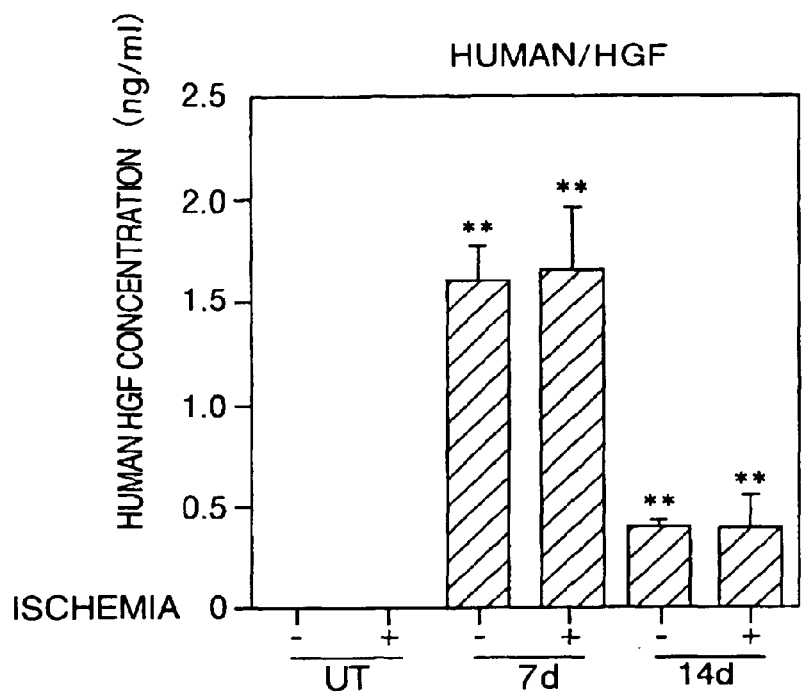
FIG. 3 is a graph showing the in vivo expression of human HGF protein in the rat cerebrospinal fluid by an ELISA method. In the figure, UT represents the rats treated with an expression vector containing no HGF gene, 7d represents the rats on day 7 after the introduction of HGF gene, and 14d represents the rats on day 14 after the introduction of HGF gene. In the figure also, − represents the absence of obstruction, and + represents the presence of obstruction in the carotid artery. The ordinate represents the concentration of HGF (ng/ml). **: $P<0.01$ for UT. n=4 for each group.
Figure 4:
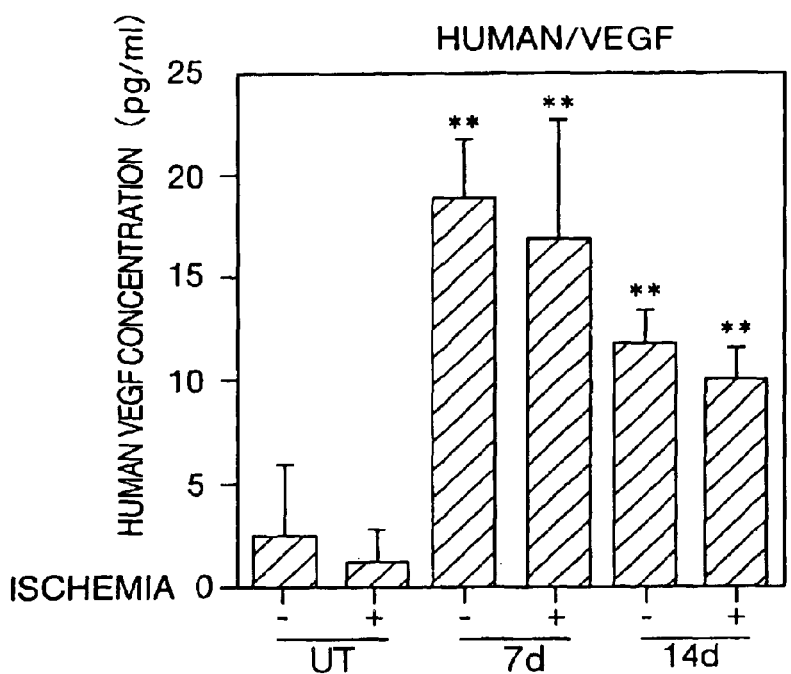
FIG. 4 is a graph showing the in vivo expression of human VEGF protein in the rat cerebrospinal fluid by an ELISA method. In the figure, UT represents the rats treated with an expression vector containing no VEGF gene, 7d represents the rats on day 7 after the introduction of VEGF gene, and 14d represents the rats on day 14 after the introduction of VEGF gene. In the figure also, − represents absence of obstruction in the carotid artery, and + represents the presence of obstruction. The ordinate represent the concentration of VEGF (pg/ml). **: $P<0.01$ for UT. n=4 for each group.

In order to understand the effect of introduction of HGF gene and VEGF gene, the protein expression of these molecules in the cerebrospinal fluid (CSF) was determined by an ELISA method (n=4, each group). First, human HGF and VEGF were determined in the CSF of the control rats (treated with an expression vector in which no HGF gene or VEGF gene were introduced) before, 7 and 14 days after the obstruction of the bilateral carotid arteries, and no concentration of these proteins was detected (FIG. 3 and FIG. 4).

Next, the concentration of human HGF protein was determined in the CSF of the rats in which HGF gene (concentration in HVJ-liposome: 20 µg/ml) was introduced into the subarachnoid space immediately after the carotid artery obstruction. On day 7 after transfection, human HGF was detected but not rat HGF (FIG. 3). There were no marked differences observe between the rats (1.63±0.16 ng/ml) in which the carotid artery was obstructed and the rats (1.67±0.29 ng/ml) in which the carotid artery was not obstructed. Even on day 14 after transfection, human HGF was detected (0.40±0.04 ng/ml) (FIG. 3).

In a similar procedure to the above HGF gene, VEGF gene (concentration in HVJ-liposome: 20 µg/ml) was introduced into the subarachnoid space, and the concentration of human VEGF in the CSF was much lower than HGF (FIG. 4) (day 7; 18.9±2.9 pg/ml for the rats in which the carotid artery was not obstructed, and 16.8±5.8 pg/ml for the rats in which the carotid artery was obstructed, day 14; 11.7±1.6 pg/ml for the rats in which the carotid artery was not obstructed, and 9.9±1.5 pg/ml for the rats in which the carotid artery was obstructed). The reason for these differences are unknown, but it appears that it is preferred to cause angiogenesis by applying HGF in order to treat chronic reduction in blood flow.

EXAMPLE 3
Angiogenesis on the Brain Surface by HGF Transfection

Figure 5:
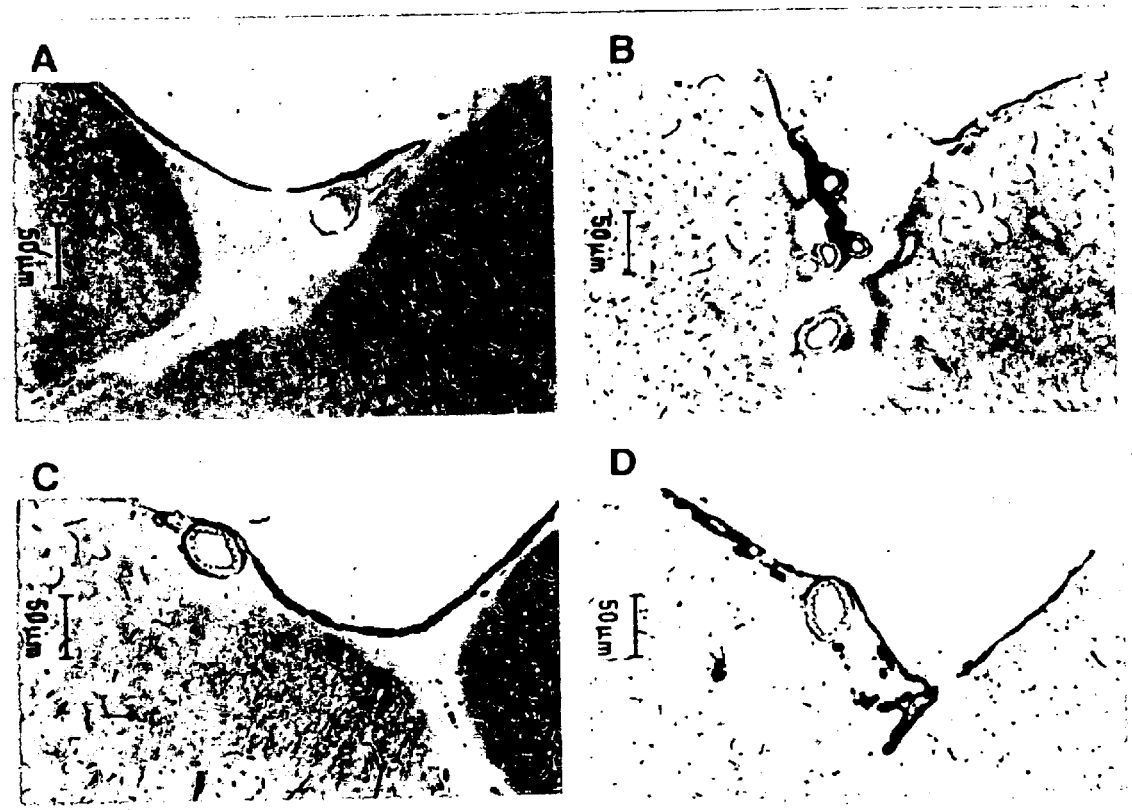
FIG. 5 is a microphotograph showing the result of cyto-histochemical staining of the endothelial cell in the brain and in its periphery before and 7 days after the transfection of HGF gene. A (upper left), a brain transfected with a vector (expression vector containing no HGF gene) without obstructing the carotid artery; B (upper right), a brain transfected with HGF gene without obstructing the carotid artery; C (bottom left), a brain transfected with a vector on day 7 after the obstruction of the carotid artery; D (bottom right), a brain transfected with HGF gene on day 7 after the obstruction of the carotid artery. n=4 for each group.

Using the tissue of the rats that were treated as in Example 2, the effect of HGF gene introduction in the CNS on angiogenesis was confirmed. Thus, by performing histopathological analysis using an alkaline phosphatase (ALP) staining that detects vascular endothelial cells, endothelial cells in and around the brain were detected. In the rats in which HGF gene was not introduced, ALP-positive cells were limited to the inside of the brain before and 7 days after the obstruction of the bilateral carotid arteries (A and C in FIG. 5). Interestingly, in the rats in which HGF gene was introduced, ALP-positive cells were observed on the brain surface, and more cells were observed on the brain surface in the rats in which the bilateral carotid arteries were obstructed than in the rats in which the bilateral carotid arteries were not obstructed (B and D in FIG. 5). These results suggested that the introduction of HGF gene caused angiogenesis in particular on the brain surface in an ischemic state.

EXAMPLE 4
Cerebral Blood Flow (CRF) in the Rat Measured by LDI

Figure 6:
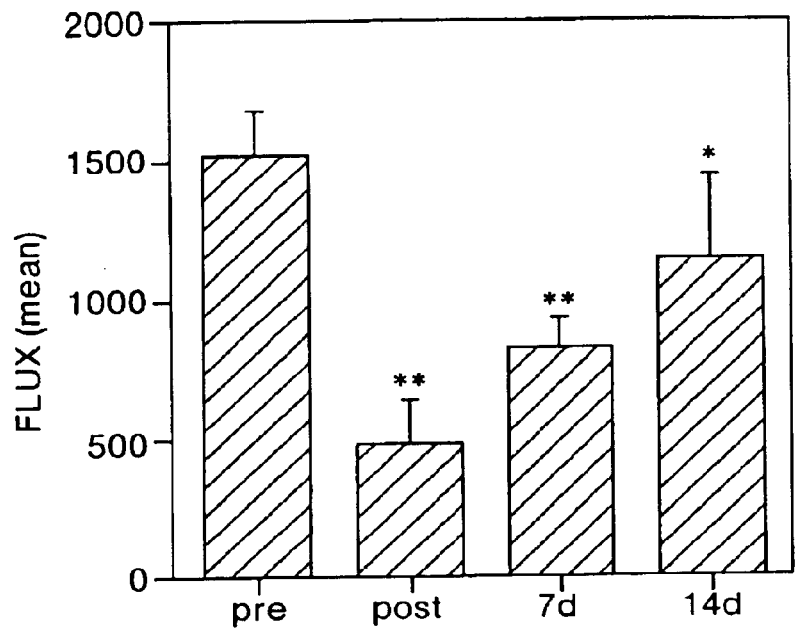
FIG. 6 is a graph showing changes in cerebral blood flow with time measured by a laser Doppler imager (LDI). In the figure, pre represents before obstruction, post represents after the obstruction of the carotid artery, 7d represents 7 days after obstruction, and 14d represents 14 days after obstruction. The ordinate (FLUX) represents an mean cerebral perfusion. Relative to pre, *P<0.05, **P<0.01. n=6 for each group.

CBF in the rat was measured before and after the obstruction of the bilateral carotid arteries. First, changes in CBF of the rats in which gene was not introduced were analyzed before, immediately after, 7 and 14 days after obstruction. As expected, CBF decreased immediately after obstruction of the bilateral carotid arteries, and gradually increased with time (FIG. 6). However, CBF was markedly lower on day 7 and 14 after obstruction compared to the non-treated rats (FIG. 6).

Figure 7:
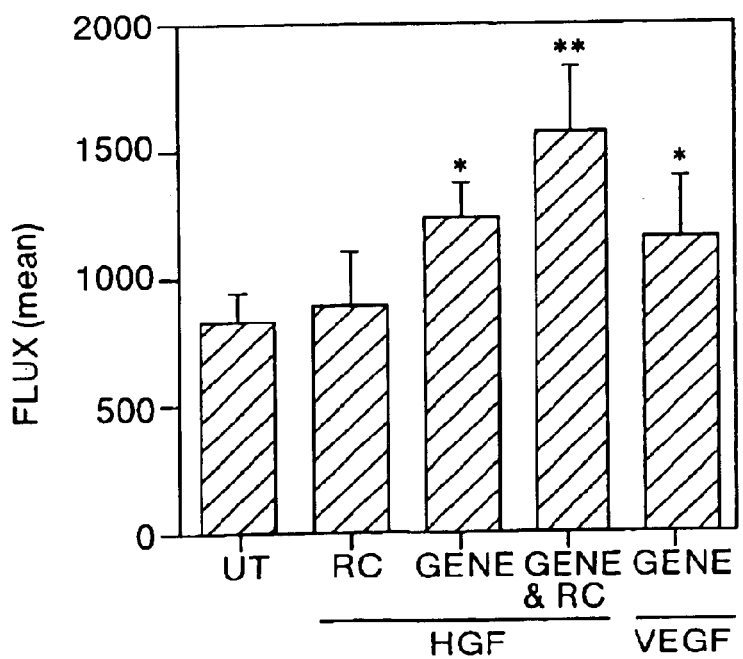
FIG. 7 is a graph showing CBF measured by LDI on day 7 after the obstruction of the carotid artery. In the figure, UP represents the rats treated with an expression vector, RC represents the rats treated with recombinant HGF (200 μg), GENE represents the rats treated with HGF gene (10 μg), GENE&RC represents the rats treated with recombinant HGF (200 μg) and HGF gene (10 μg), and GENE in VEGF represents the result of the rats treated with VEGF gene (20 μg/ml). The ordinate (FLUX) is an mean cerebral perfusion. Relative to pre, *P<0.05, **P<0.01. n=6 for each group.

Next, the rats treated with recombinant HGF (200 µg), HGF gene (concentration in HVJ-liposome: 20 µg/ml), and a combination of recombinant HGF and HGF gene were measured. The HGF gene and recombinant HGF were injected to the subarachnoid space in a manner similar to that in Examples 2 and 3. Each treatment was performed 10 minutes after carotid artery obstruction. In the rats treated with recombinant HGF, no marked increases in CBF were observed compared to the control rats (control: 886.1±99.6, recombinant HGF: 985.5±142.4) (FIG. 7). However, in the treatment with HGF gene introduction, CBF showed a marked increase on day 7 after obstruction (1214.5±145.1). Furthermore, in the rats treated with a combination of recombinant HGF and gene introduction, unexpectedly, CBF was much higher on day 7 compared to gene introduction alone (1490.3±197.9). These results demonstrated that angiogenesis by the introduction of HGF gene improves chronic reduction in cerebral blood flow, and that the combination of the gene and recombinant HGF is the most effective when treated after arterial obstruction.

On the other hand, since VEGF gene also enhanced CBF (1122.8±265.3) (FIG. 7), VEGF gene was also shown to be effective in improving reduced blood flow in the brain.

Figure 8:
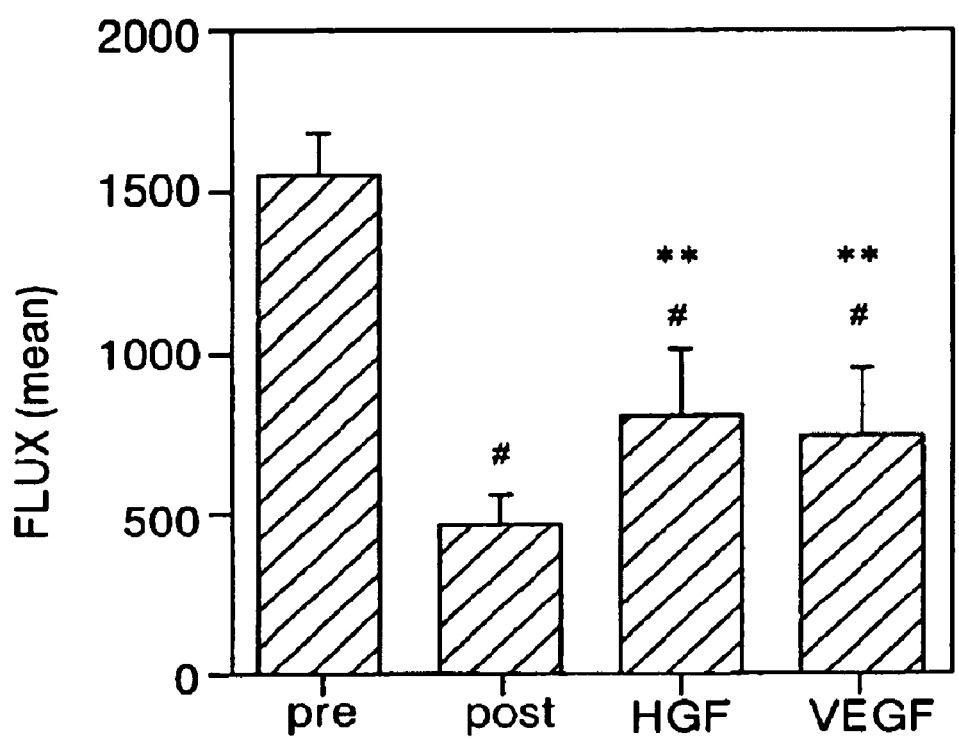
FIG. 8 is a graph showing CBF measured by LDI before and immediately after the obstruction of the carotid artery. In the figure, pre represents before the obstruction of the carotid artery of the control rats, post represents immediately after the obstruction of the carotid artery, HGF represents the result of the rats immediately after carotid artery obstruction that were subjected to HGF transfection 7 days before arterial obstruction, and VEGF represents the result of the rats immediately after carotid artery obstruction that were subjected to VEGF transfection 7 days before arterial obstruction. Relative to post, **P<0.01. n=5 for each group.

Next, the effectiveness of the treatment was investigated when it was performed before arterial obstruction. Interestingly, the treatment with HGF gene or VEGF gene before arterial obstruction prevented reduction in CBF due to carotid artery obstruction (control: 459.4±97.4, HGF: 796.8±204, VEGF: 737.6±211.5) (FIG. 8). These results indicate that when delivered before ischemia, the introduction of HGF gene and VEGF gene is effective in preventing reduced blood flow due to arterial obstruction.

Experiment II.

Study on the Suppressive Effect of Neuronal Death in the Brain by HGF Gene

Experimental Method

The HVJ-liposome complex containing human HGF gene and human recombinant HGF used in the experiment were prepared in the same manner as in the above Experiment I.

In the experiment, male Mongolian gerbils (weight: 50–70 g) were used. The animals were bred in a room of which temperature was maintained at 24° C. and water and the feed were given ad libitum. The Mongolian gerbils were divided into five groups. "sham": the control group (group with no ischemic stimulation), "vehicle": the group with 5-min ischemia of the bilateral carotid arteries, "post G": the group with HGF gene introduction after 5-min ischemia of the bilateral carotid arteries, "pre G": the group with HGF gene introduction before 5-min ischemia of the bilateral carotid arteries. "post R": the group with one-time administration of recombinant HGF gene after 5-min ischemia of the bilateral carotid arteries. Wearing a face mask, anesthesia of 3% halothane was performed, and maintained at a mixed air of 1.5% halothane, 20% oxygen, and 80% nitrogen. Body temperature (the temperature of the rectum) was always monitored to maintain at around 37° C. using a heat pad. After the bilateral carotid arteries were exposed, blood flow was completely blocked using a blood vessel clip for 5 minutes. Thereafter, the clip was released to restore blood flow. Immediately before or immediately after the surgical treatment, human HGF gene (20 $\mu$g) was introduced from the subarachnoid space to the cerebrospinal cavity using the HVJ-liposome method. Recombinant HGF (30 $\mu$g) was given from the subarachnoid space to cerebrospinal cavity immediately after the surgical treatment. After the surgery also, the cage was maintained at 37° C. to wait for recovery to occur. The control group was treated in the same manner as in the other groups except blood flow blocking. On day 4 and 7 after ischemia, the brain was extracted and the sections were HE stained, TUNEL stained, and immunostained before performing histopathological analysis. The concentration of HGF in the cerebrospinal fluid was measured using a human HGF ELISA analysis.

Based on the above experimental method, the following Example 5 was performed.

EXAMPLE 5

Figure 9:
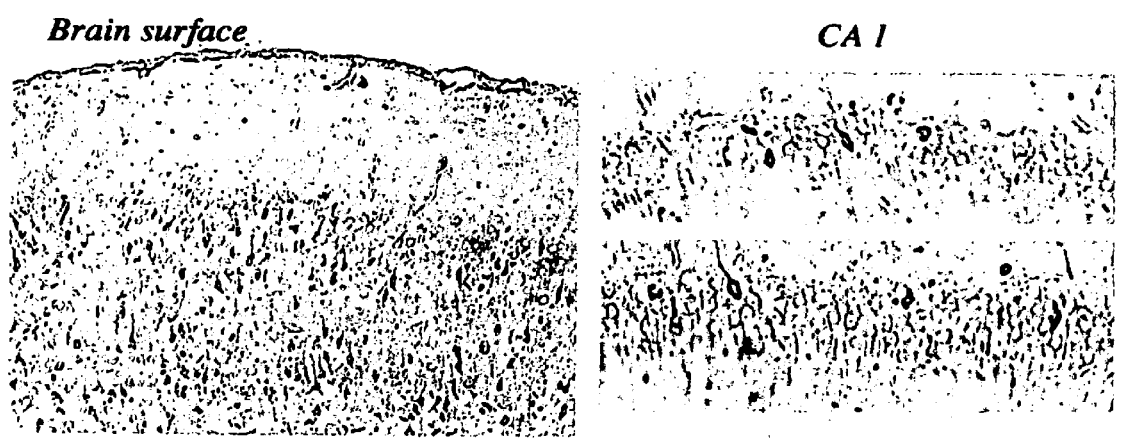
FIG. 9 is a microphotograph showing the expression of β-gal (β-galactosidase) on the brain surface (brain surface in the figure) and in the hippocampus CA-1 region (CA1 in the figure).

Suppression of Neuronal Death in the Hippocampus CA-1 Region by HGF Gene Transfection Using normal Mongolian gerbils, the introduction of gene from the subarachnoid space to the cerebrospinal cavity by the HVJ-liposome method was confirmed. When β-galactosidase gene was introduced and the sections of the brain were β-gal stained, gene expression was observed on the brain surface and the hippocampus CA-1 region (FIG. 9).

Figure 10:
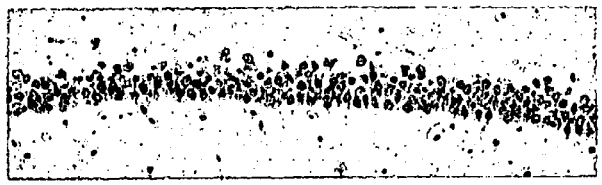
FIG. 10 is a microphotograph showing the result in which delayed neuronal death was observed in the hippocampus CA-1 region by ischemic stimulation of the bilateral carotid arteries. In the figure, Sham ope. 7 days represents the result on day 7 of the control (surgically treatment only without ischemic stimulation), and Vehicle (4 days, 7 days) represents the result on day 4 and 7 after ischemia of the bilateral carotid arteries, respectively.
Figure 10:
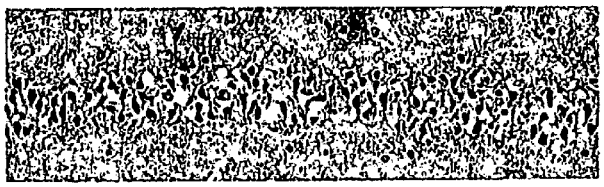
Figure 10:
Figure 11:
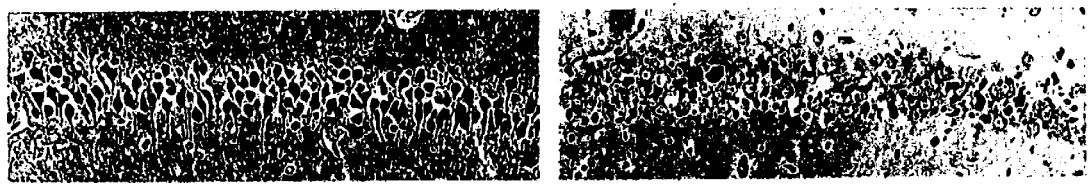
FIG. 11 is a microphotograph showing the result in which delayed neuronal death in the hippocampus CA-1 region was suppressed by the introduction of HGF gene or recombinant HGF protein before and after ischemic stimulation of the bilateral carotid arteries. In the figure, Post HGF gene (4 days, 7 days) represents the result on day 4 and day 7 in which HGF gene was introduced immediately after ischemia of the bilateral carotid arteries, Pre HGF gene 7 days represents the result on day 7 in which HGF gene was introduced immediately before ischemia of the bilateral carotid arteries, and r-HGF 7 days represents the result on day 7 in which recombinant HGF protein was introduced immediately after ischemia of the bilateral carotid arteries.
Figure 11:
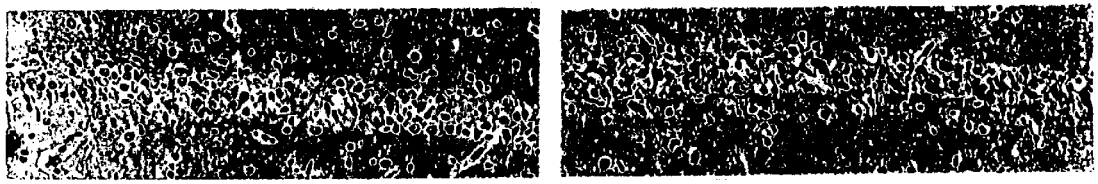
Figure 12:
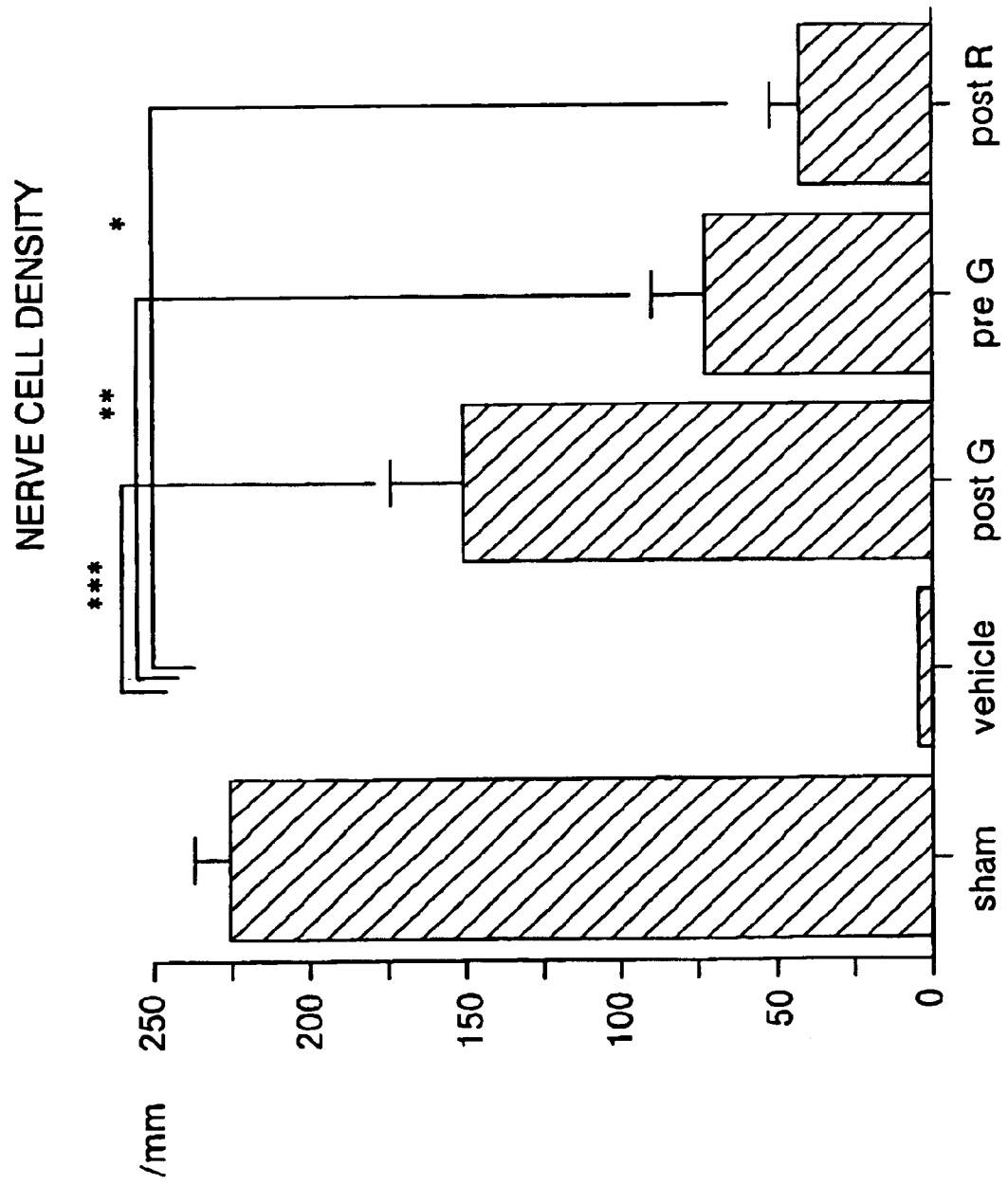
FIG. 12 is a graph showing the result in which the density of nerve cells in the hippocampus CA-1 region was measured by staining the live nerve cells. In the figure, the ordinate represents the cell density (live nerve cell count/mm). Sham in the abscissa represents the result of the control (no ischemic stimulation), vehicle represents the result of ischemia of the bilateral carotid arteries, PostG represents the result in which HGF gene was introduced immediately after ischemia of the bilateral carotid arteries, PreG represents the result in which HGF gene was introduced before ischemia of the bilateral carotid arteries, and PostR represents the result in which recombinant HGF protein was introduced after ischemia of the bilateral carotid arteries. Relative to vehicle, *P<0.05, P<0.01, and *P<0.001.
Figure 13:
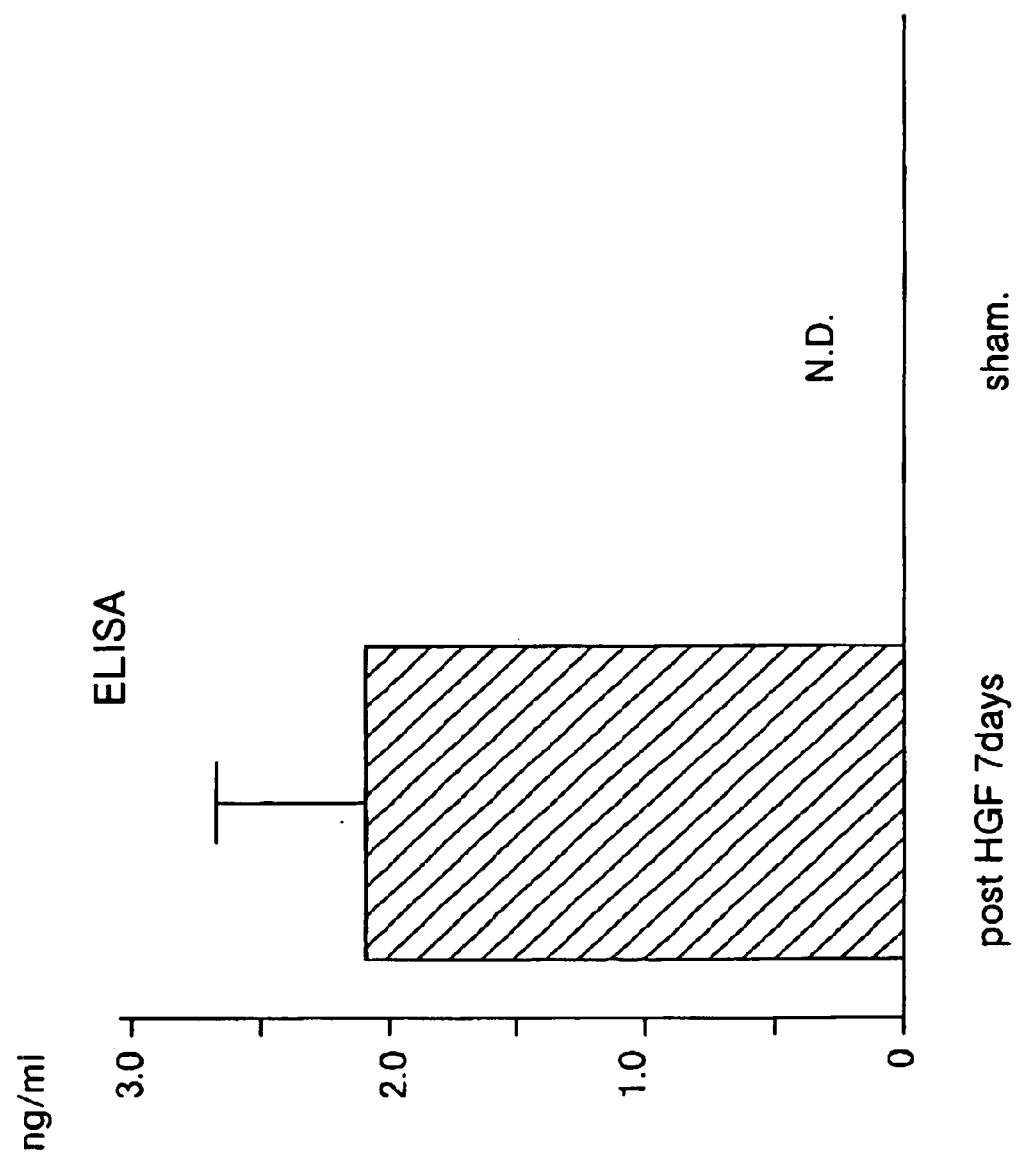
FIG. 13 is a graph showing the result in which HGF gene was introduced after ischemia of the bilateral carotid arteries and then the protein concentration of HGF in the cerebrospinal fluid 7 days later was measured by an ELISA method. In the figure, the ordinate represents the protein concentration (ng/ml) of HGF, post HGF on the abscissa represents the result of introduction of HGF gene, and sham represents the result of the control (no ischemic stimulation). N.D. represents the result not detected.

By ischemia for 5 minutes at the bilateral carotid arteries, delayed neuronal death was observed in the hippocampus CA-1 region of the brain (FIG. 10, the vehicle group). In contrast, the administration of HGF gene (the PreG group and the PostG group) or recombinant HGF (the PostR group) significantly suppressed delayed neuronal death (FIG. 11 and FIG. 12). When HGF concentration in the cerebrospinal fluid of the PostG group was measured by an ELISA method, HGF expression was observed even after 7 days (FIG. 13). Thus, HGF was found to be effective in suppressing delayed neuronal death due to cerebral ischemia.

Figure 14:
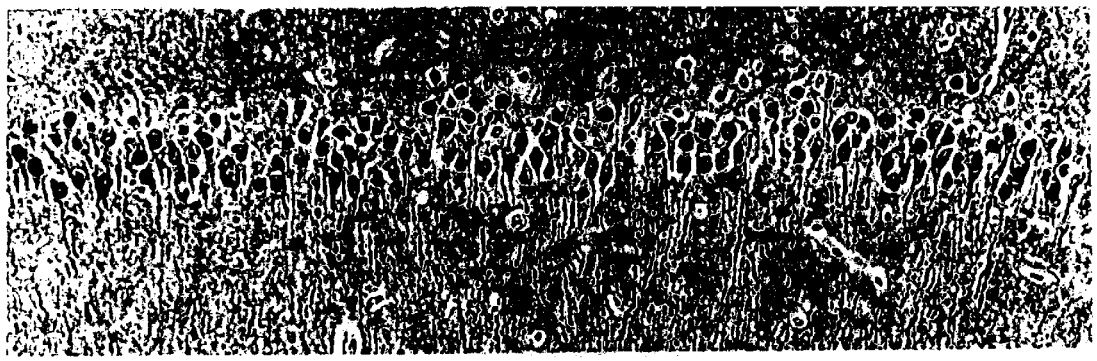
FIG. 14 is a microphotograph showing the result in which the expression of C-Met in the hippocampus CA-1 region was analyzed by an immunostaining method.

When the expression site of a HGF receptor, c-Met, was investigated by an immunostaining method, expression was observed in the CA-1 region indicating that HGF signals are transmitted through c-Met (FIG. 14).

Figure 15:
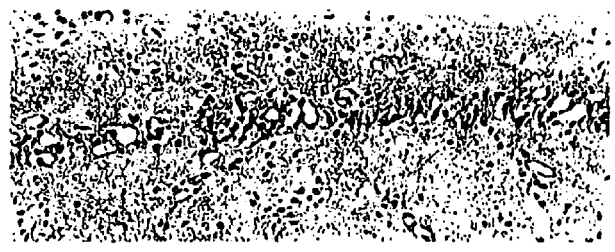
FIG. 15 is a microphotograph showing the result in which the nerve cells that had apoptosis in the hippocampus CA-1 region were stained by the TUNEL method. In the figure, DND 7 days represents the nerve cells that had delayed neuronal death on day 7 after ischemia of the bilateral carotid arteries, Post HGF gene 7 days represents the result on day 7 after HGF gene was introduced immediately after ischemia of the bilateral carotid arteries, and Pre HGF gene 7 days represents the result on day 7 after HGF gene was introduced immediately before ischemia of the bilateral carotid arteries.
Figure 15:
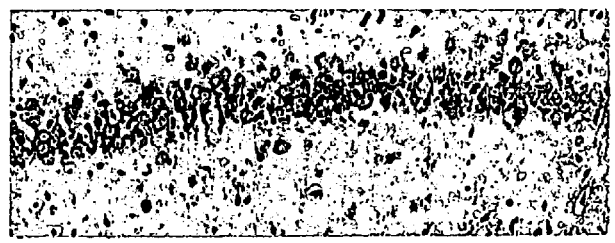
Figure 15:
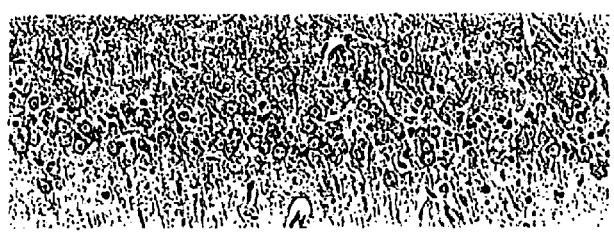
Figure 16:
FIG. 16 is a microphotograph showing the result in which the expression of Bcl-xL in the hippocampus CA-1 region was analyzed by an immunostaining method. In the figure, sham. represents the result of the control (no ischemic stimulation), post HGF (4 days, 7 days) represents the result on day 4 and day 7 after HGF gene was introduced immediately after ischemia of the bilateral carotid arteries.
Figure 16:
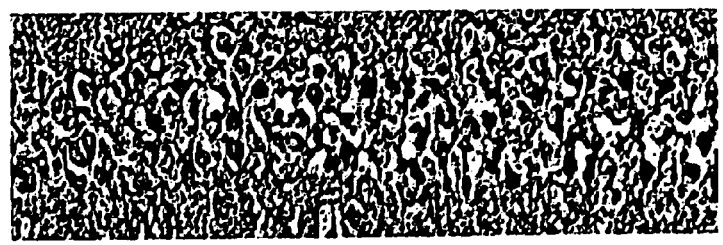
Figure 16:
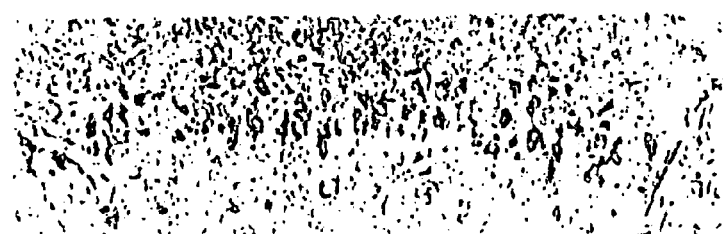
Figure 17:
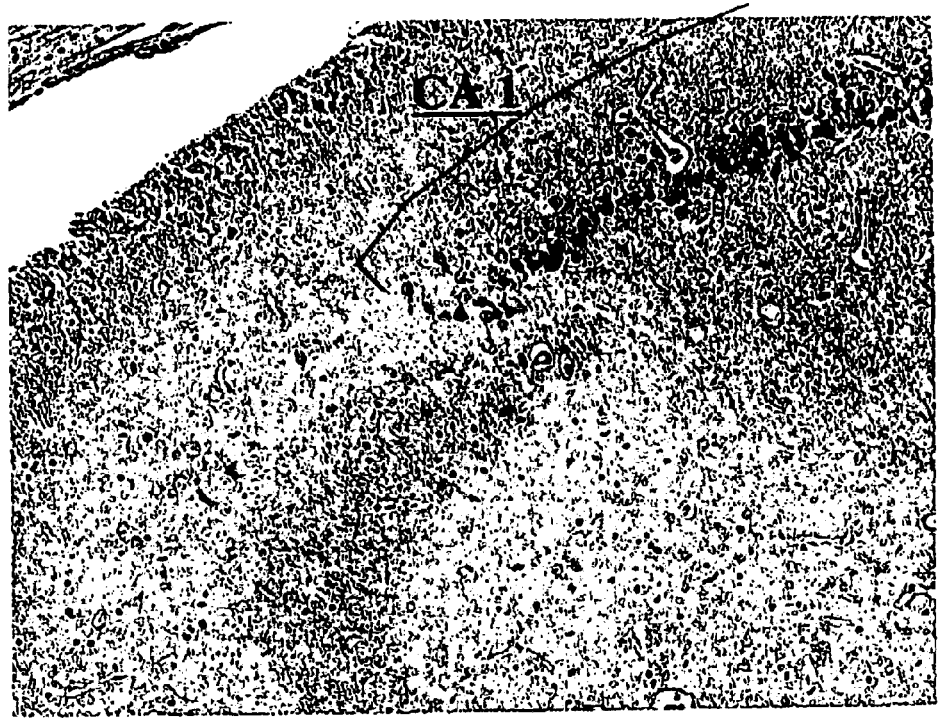
FIG. 17 is a microphotograph showing the result in which HSP70 expression In the hippocampus CA-1 region on day 7 after the introduction of HGF gene immediately after ischemia of the bilateral carotid arteries was analyzed by an immunostaining method.
Figure 18:
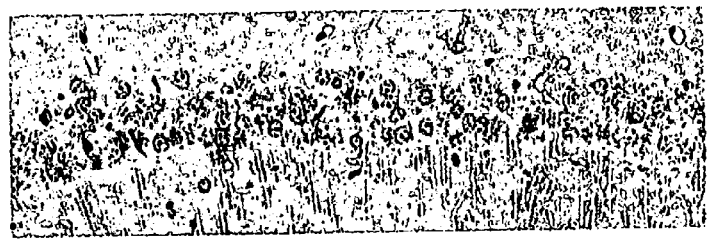
FIG. 18 is a microphotograph showing the result in which HSP70 expression in the hippocampus CA-1 region was analyzed by an immunostaining method. In the figure, Sham. represents the result of the control (no ischemic stimulation), and Post HGF 7 D represents the result on day 7 after the introduction of HGF gene immediately after ischemia of the bilateral carotid arteries.
Figure 18:

Furthermore, when nerve cells that had apoptosis in the CA-1 region were stained by the TUNEL method, apoptosis of nerve cells was observed in abundance in the vehicle group (FIG. 15). In contrast, little apoptosis was detected in the HGF gene administration group (the PreG group and the PostG group) (FIG. 15). Thus, the administration of HGF gene was thought to suppress apoptosis of nerve cells. In order to investigate the mechanism of suppression, expression in the CA-1 region of Bcl-xl and HSP70 having a apoptosis-suppressing effect was examined by immunostaining. The expression of Bcl-xL is shown in FIG. 16, and that of HSP70 is shown in FIG. 17 and FIG. 18. Expression of both proteins was confirmed in nerve cells by the administration of HGF gene. The foregoing revealed that the administration of HGF gene induces the expression of Bcl-xL and HSP70 and suppresses the apoptosis of nerve cells.

INDUSTRIAL APPLICABILITY

In accordance with the present invention, there may be provided novel therapeutic or preventive agents for cerebrovascular disorders comprising HGF gene and/or VEGF gene as an active ingredient, and novel administration methods comprising administering said therapeutic or preventive agents to the subarachnoid space.

What is claimed is:

1. A therapeutic or preventive method for cerebrovascular disorders comprising introducing into a human subject a polynucleotide encoding hepatocyte growth factor (HGF) and/or a polynucleotide encoding vascular endothelial growth factor (VEGF) in the form of hemagglutinating virus of Japan (HVJ)-liposomes by direct injection into the subarachnoid space of said subject thereby treating or preventing said cerebrovascular disorders.

2. A therapeutic or preventive method for treating or preventing reduced blood flow comprising introducing into a human subject a polynucleotide encoding HGF and/or a polynucleotide encoding VEGF in the form of HVJ-liposomes by direct injection into the subarachnoid space of said subject thereby treating or preventing said reduced blood flow.

3. A method of promoting cerebral angiogenesis comprising introducing into a human subject a polynucleotide encoding HGF and/or a polynucleotide encoding VEGF in the form of HVJ-liposomes by direct injection into the subarachnoid space of said subject thereby promoting said cerebral angiogenesis.

4. A method of suppressing neuronal death in the brain comprising introducing into a human subject a polynucleotide encoding HGF in the form of HVJ-liposomes by direct injection into the subarachnoid space of said subject thereby suppressing said neuronal death in the brain.

5. A method of suppressing apoptosis of nerve cells in the brain comprising introducing into a human subject a polynucleotide encoding HGF in the form of HVJ-liposomes by direct injection into the subarachnoid space of said subject thereby suppressing said apoptosis of nerve cells.

* * * * *

UNITED STATES PATENT AND TRADEMARK OFFICE
CERTIFICATE OF CORRECTION

PATENT NO. : 6,936,594 B1
DATED : August 30, 2005
INVENTOR(S) : Ryuichi Morishita et al.

It is certified that error appears in the above-identified patent and that said Letters Patent is hereby corrected as shown below:

Title page,
Item [73], should read:
-- [73] Assignee: AnGes MG, Inc., Osaka (JP) --.

Signed and Sealed this

Twenty-third Day of May, 2006

JON W. DUDAS
*Director of the United States Patent and Trademark Office*